United States Patent [19]

Komiyama et al.

[11] Patent Number: 5,082,972
[45] Date of Patent: Jan. 21, 1992

[54] PROCESS FOR PREPARATION OF ACYCLIC ETHYLENEAMINES

[75] Inventors: Tadashi Komiyama; Hisaharu Kuboyama; Takashi Jimbo; Hiroyoshi Watanabe; Shuichi Tokumoto; Yumiko Endoh; Eiichi Sugiyama; Yoshitaro Naganuma, all of Kanagawa, Japan

[73] Assignee: Mitsui Toatsu Chemicals, Inc., Tokyo, Japan

[21] Appl. No.: 551,086

[22] Filed: Jul. 11, 1990

[30] Foreign Application Priority Data

| Jul. 17, 1989 [JP] | Japan | 1-182466 |
| Jul. 18, 1989 [JP] | Japan | 1-183590 |
| Jul. 25, 1989 [JP] | Japan | 1-190470 |
| Jul. 25, 1989 [JP] | Japan | 1-190472 |

[51] Int. Cl.$^5$ .................................. C07C 209/68
[52] U.S. Cl. .................. 564/480; 564/479; 564/512
[58] Field of Search ............ 564/479, 480, 512

[56] References Cited

U.S. PATENT DOCUMENTS

| 2,758,097 | 8/1986 | Doherty et al. |
| 3,716,545 | 2/1973 | Ripley. |
| 4,394,524 | 7/1983 | Ford et al. ............ 564/479 |
| 4,547,591 | 10/1985 | Brennan et al. ........ 564/479 |

FOREIGN PATENT DOCUMENTS 2147896A 5/1985 United Kingdom.

Primary Examiner—Marianne Cintins
Assistant Examiner—Jessica H. Nguyen
Attorney, Agent, or Firm—Burns, Doane, Swecker & Mathis

[57] ABSTRACT

At least one of ammonia and ethylenediamine is reacted with monoethanolamine in the presence of a catalyst containing phosphoric acid or its condensate in order to prepare acyclic ethyleneamines, and the catalyst can be improved in performance and the life of the catalyst can be prolonged by feeding a phosphorus-containing material to a reaction system during the reaction. In addition, the catalyst having a deteriorated performance can be reactivated by adding the phosphorus-containing material to the catalyst.

2 Claims, No Drawings

PROCESS FOR PREPARATION OF ACYCLIC ETHYLENEAMINES

BACKGROUND OF THE INVENTION (i) Field of the Invention

The present invention relates to a process for the preparation of acyclic ethyleneamines by reacting at least one of ammonia and ethylenediamine with monoethanolamine, and it also relates to a process for reactivating a catalyst having a deteriorated performance which has been used in the above-mentioned reaction.

(ii) Description of the Prior Art

Ethyleneamines have been heretofore manufactured by reacting 1,2-dichloroethane with ammonia or reacting monoethanolamine with ammonia in the presence of a hydrogenation catalyst [Isao Ono, Chemical Economics, No. 6, p. 20–27 (1979)]. In the former process, sodium chloride as a by-product is produced in an amount of up to twice the molar amount of ethylenediamine and vinyl chloride monomer is also secondarily produced, which means that a great cost is required to dispose of these by-products. In addition, an apparatus to be used tends to be appreciably corroded with chlorine ions. In the latter process referred to above, useless cyclic amines are produced in an amount of up to 20%, and for this reason, the aforesaid process is also unsatisfactory to manufacture the useful acyclic ethyleneamines.

In recent years, another process for the manufacture of ethyleneamines has been reported which comprises the step of reacting ammonia or ethylenediamine with monoethanolamine in the presence of a phosphorus-containing material (e.g., Japanese Laid-open Patent Publication Nos. 61-183249, 51-147600 and 60-78945). However, the catalyst (phosphorus-containing material) used in this process has a drawback that its life is short, though the selectivity of the acyclic ethyleneamines is high.

SUMMARY OF THE INVENTION

An object of the present invention is to provide a process which comprises reacting at least one of ammonia and ethylenediamine with monoethanolamine to prepare acyclic ethyleneamines stably for a long period of time.

Another object of the present invention is to provide a process for reactivating a catalyst having a deteriorated performance which has been used in the aforesaid reaction.

Still another object of the present invention is to provide an industrially very valuable process for preparing acyclic ethyleneamines from ammonia or ethylenediamine and monoethanolamine in high yields.

According to one aspect of the present invention, there is provided a process for the preparation of acyclic ethyleneamines which comprises reacting raw materials in the presence of a catalyst containing phosphoric acid or its condensate, while a phosphorus-containing material is fed to the reaction system.

According to another aspect of the present invention, there is provided a process for the preparation of acyclic ethyleneamines which comprises reacting raw materials in the presence of a catalyst containing phosphoric acid or its condensate which has been reactivated by adding a phosphorus-containing material thereto.

According to still another aspect of the present invention, there is provided a process for reactivating a catalyst containing phosphoric acid or its condensate for the preparation of acyclic ethyleneamines which comprises adding a phosphorus-containing material to the catalyst having a deteriorated performance which has been used in the reaction of raw materials.

DESCRIPTION OF THE PREFERRED EMBODIMENTS

In the first place, reference will be made to the first aspect of the present invention.

Examples of a catalyst containing phosphoric acid or its condensate used in the present invention include catalysts prepared by causing phosphoric acid, pyrophosphoric acid, triphosphoric acid, polyphosphoric acid, ammonium phosphate, ammonium pyrophosphate and ammonium triphosphate to be supported on carriers such a silica, alumina, silica-alumina, diatomaceous earth and clay as well as metallic salts of phosphoric acid, pyrophosphoric acid, triphosphoric acid and polyphosphoric acid. Typical examples of the metal salts of phosphoric acid include salts of metals (Group IIa of the periodic table) of phosphoric acid such as beryllium dihydrogenphosphate, magnesium dihydrogenphosphate, calcium dihydrogenphosphate, strontium dihydrogenphosphate, barium dihydrogenphosphate, beryllium monohydrogenphosphate, magnesium monohydrogenphosphate, calcium monohydrogenphosphate, strontium monohydrogenphosphate, barium monohydrogenphosphate, beryllium phosphate, magnesium phosphate, calcium phosphate, strontium phosphate, and barium phosphate. Reaction products of compounds of metals in the group IIIa of the periodic table and phosphoric acid in which the P/metal atomic ratio is from 1 to 6. For example, they include reaction products of phosphoric acid and hydroxides or oxides of scandium, yttrium, lanthanum, cerium, praseodymium, neodymium, samarium, europium, gadolinium, terbium, dysprosium, holmium, erbium, thulium, ytterbium and lutetium.

The above-mentioned metal salts of phosphoric acid also include reaction products of compounds of metals in the group IVa of the periodic table and phosphoric acid in which the P/metal atomic ratio is from 1 to 6, and for example, they are reaction products of phosphoric acid and hydroxides or oxides of titanium, zirconium and hafnium. Typical known examples of the reaction products include titanium monohydrogenphosphate, zirconium monohydrogenphosphate and hafnium monohydrogenphosphate.

The above-mentioned metal salts of phosphoric acid also include reaction products of compounds of metals in the group Va of the periodic table and phosphoric acid in which the P/metal atomic ratio is from 1 to 6, and for example, they are reaction products of phosphoric acid and hydroxides or oxides of vanadium, niobium and tantalum. Typical known examples of the reaction product include vanadyl dihydrogenphosphate (P/V atomic ratio=2) and the like.

Moreover, the above-mentioned usable metal salts of phosphoric acid also include salts of pyrophosphoric acid, triphosphoric acid and polyphosphoric acid and metals in the groups IIa, IIIa, IVa and Va of the periodic table mentioned in the above paragraphs.

Examples of the phosphorus-containing material used in the process of the present invention include phosphoric acid, phosphorous acid, phosphates, phosphites, phosphoric esters, phosphorous esters, pyrophosphoric acid, triphosphoric acid, polyphosphoric acid, pyrophosphates, triphosphates and pyrophosphoric esters.

The above-mentioned phosphates, phosphites, pyrophosphates and triphosphates are preferably ammonium salts. Furthermore, the above-mentioned phosphoric esters, phosphorous esters and pyrophosphoric esters are preferably esters of their corresponding acids and alcohols having 1 to 4 carbon atoms. Examples of the phosphoric esters include monomethyl phosphate, dimethyl phosphate, trimethyl phosphate, monoethyl phosphate, diethyl phosphate, triethyl phosphate, monopropyl phosphate, dipropyl phosphate, tripropyl phosphate, monobutyl phosphate, dibutyl phosphate and tributyl phosphate. Examples of the phosphorous esters include monomethyl phosphite, dimethyl phosphite, trimethyl phosphite, monoethyl phosphite, diethyl phosphite, triethyl phosphite, monopropyl phosphite, dipropyl phosphite, tripropyl phosphite, monobutyl phosphite, dibutyl phosphite and tributyl phosphite. Furthermore, examples of the pyrophosphoric ester include tetraethyl pyrophosphate.

These phosphorus-containing materials can be used singly or in the form of a mixture of two or more thereof. The particularly preferable phosphorus-containing materials are phosphoric acid, phosphorous acid, pyrophosphoric acid, ammonium phosphate, ammonium phosphite, ammonium pyrophosphate, monoethyl phosphate, diethyl phosphate and triethyl phosphate.

The amount of the phosphorus-containing material to be fed is from 1 to 10,000 ppm by weight, preferably 10 to 1,000 ppm by weight, in terms of P with respect to 1 part by weight of monoethanolamine which is one of the reaction materials. When the amount of the phosphorus-containing material is less than 1 ppm by weight, its effects (improvement of the performance and the like) are poor. On the other hand, the amount of 10,000 ppm by weight is enough to exert the effects, and the addition of more than this level is usually unnecessary.

The raw materials used in the process of the present invention are monoethanolamine and at least one of ammonia and ethylenediamine.

When ammonia is reacted with monoethanolamine, there are usually produced ethylenediamine, diethylenetriamine, triethylenetetramine and the like. When ethylenediamine is reacted with monoethanolamine, there are usually produced diethylenetriamine, triethylenetetramine and the like. When ammonia, ethylenediamine and monoethanolamine are reacted, there are usually produced ethylenediamine, diethylenetetramine, triethylenetetramine, tetraethylenepentamine and the like.

In reacting ammonia with monoethanolamine in accordance with the process of the present invention, the molar ratio of ammonia/monoethanolamine is usually adjusted to 1 or more. When the reaction is carried out at an ammonia/monoethanolamine ratio of less than 1, cyclic materials such as piperazine and aminoethylpiperazine are produced in large quantities. Preferably, the reaction is effected by adjusting this molar ratio so as to be in the range of from 6 to 50. The higher the molar ratio is, the smaller the amount of the produced cyclic materials is, but its production efficiency deteriorates.

In reacting ethylenediamine with monoethanolamine, the molar ratio of ethylenediamine/monoethanolamine is usually adjusted to 0.1–10. When the reaction is carried out at an ethylenediamine/monoethanolamine ratio of less than 0.1, cyclic materials such as piperazine and aminoethylpiperazine are produced in large quantities. Preferably, the reaction is effected by adjusting this molar ratio to be in the range of from 1 to 5. The higher the molar ratio is, the smaller the amount of the produced cyclic materials is, but its production efficiency deteriorates.

In the reaction of ammonia, ethylenediamine and monoethanolamine, the molar ratio of ammonia/monoethanolamine is usually adjusted to 1 or more. When the reaction is carried out at an ammonia/monoethanolamine ratio of less than 1, cyclic materials such as piperazine and aminoethylpiperazine are produced in large quantities. Preferably, the reaction is effected by adjusting this molar ratio to be in the range of from 6 to 50. The higher the molar ratio is, the smaller the amount of the produced cyclic materials is, but its production efficiency deteriorates. Alternatively, the reaction is carried out usually by adjusting ethylenediamine/monoethanolamine to 0.01–10. The higher this molar ratio is, the smaller the net amount of ethylenediamine produced by reacting ammonia with monoethanolamine is and the larger the amounts of produced diethylenetriamine, triethylenetetramine, tetraethylenepentamine and the like are. Preferably, the reaction is effected by adjusting this molar ratio to be in the range of from 0.05 to 5.

In each of the above-mentioned reactions, the reaction temperature is from 150° to 400° C. When the temperature is less than 150° C., the reaction rate is low, and when it is in excess of 400° C., the produced ethyleneamines are liable to thermally decompose. The preferable reaction temperature is in the range of 200° to 350° C.

The reaction pressure is usually in the range of 20 to 1,000 kg/cm$^2$, when ammonia is reacted with monoethanolamine. The higher the pressure is, the higher the selectivity of the acyclic ethyleneamines is. In case ethylenediamine is reacted with monoethanolamine, the pressure is usually from 1 to 200 kg/cm$^2$.

In the case of the reaction of ammonia, ethylenediamine and monoethanolamine, the reaction pressure is usually from 1 to 1,000 kg/cm$^2$. The higher the pressure is, the higher the selectivity of the acyclic ethyleneamines is.

The feed rate of the raw materials is from 0.1 to 30 g of the total materials per gram of the catalyst per hour, preferably from 0.2 to 10 g of the total materials per gram of the catalyst per hour.

The process of the present invention may use a fixed bed system.

The catalyst may be supported on a material such as silica, alumina, silica-alumina, diatomaceous earth, clay and the like. In case a reaction product obtained from phosphoric acid and a titanium compound is used as the catalyst, it is preferred that the strength of the catalyst is increased by using the carrier, the suitable material of which is silica.

The separation of the products from the reaction solution can be easily effected by, for example, distillation. In this case, separated ammonia, ethylenediamine and monoethanolamine can be returned to the reaction vessel and then reused therein.

Next, the second and third aspects of the present invention will be described.

The catalyst containing phosphoric acid or its condensate, the phosphorus-containing material and the reaction materials are as defined above.

The reaction process of the second and third aspects of the present invention is slightly different from that of the first aspect thereof.

In reacting ammonia with monoethanolamine in accordance with the process of the present invention, the molar ratio of ammonia/monoethanolamine is usually adjusted to 1 or more. When the reaction is carried out at an ammonia/monoethanolamine ratio of less than 1, cyclic materials such as piperazine and aminoethylpiperazine are produced in large quantities. Preferably, the reaction is effected by adjusting this molar ratio so as to be in the range of from 6 to 50. The higher the molar ratio is, the smaller the amount of the produced cyclic materials is, but its production efficiency deteriorates.

In reacting ethylenediamine with monoethanolamine, the molar ratio of ethylenediamine/monoethanolamine is usually adjusted to 0.1-10. When the reaction is carried out at an ethylenediamine/monoethanolamine ratio of less than 0.1, cyclic materials such as piperazine and aminoethylpiperazine are produced in large quantities. Preferably, the reaction is effected by adjusting this molar ratio to be in the range of from 1 to 5. The higher the molar ratio is, the smaller the amount of the produced cyclic materials is, but its production efficiency deteriorates.

In the reaction of ammonia, ethylenediamine and monoethanolamine, the molar ratio of ammonia/monoethanolamine is usually adjusted to 1 or more. When the reaction is carried out at an ammonia/monoethanolamine ratio of less than 1, cyclic materials such as piperazine and aminoethylpiperazine are produced in large quantities. Preferably, the reaction is effected by adjusting this molar ratio to be in the range of from 6 to 50. The higher the molar ratio is, the smaller the amount of the produced cyclic materials is, but its production efficiency deteriorates. Alternatively, the reaction is carried out usually by adjusting ethylenediamine/monoethanolamine to 0.01-10. The higher this molar ratio is, the smaller the net amount of ethylenediamine produced by reacting ammonia with monoethanolamine is and the larger the amounts of produced diethylenetriamine, triethylenetetramine, tetraethylenepentamine and the like are. Preferably, the reaction is effected adjusting this molar ratio to be in the range of from 0.05 to 5.

In each of the above-mentioned reactions, the reaction temperature is from 150° to 400° C. When the temperature is less than 150° C., the reaction rate is low, and when it is in excess of 400° C., produced ethyleneamines are liable to thermally decompose. The preferable reaction temperature is in the range of 200° to 350° C.

The reaction pressure is usually in the range of 1 to 1,000 kg/cm$^2$, when ammonia is reacted with monoethanolamine. The higher the pressure is, the higher the selectivity of the acyclic ethyleneamines is. In case ethylenediamine is reacted with monoethanolamine, the pressure is usually from 1 to 200 kg/cm$^2$.

In the case of the reaction of ammonia, ethylenediamine and monoethanolamine, the reaction pressure is usually from 1 to 1,000 kg/cm$^2$. The higher the pressure is, the higher the selectivity of the acyclic ethyleneamines is.

The reaction can be effected by using either of a batch system and a continuous system.

In the case of the batch system, the amount of the recovered catalyst is from 0.01 to 1 mole in terms of a phosphorus element with respect to 1 mole of ethanolamine. When the amount of the catalyst is less than 0.01 mole, the reaction rate is low. The amount of 1 mole can provide a sufficient reaction rate, and so the addition of more than this level is usually unnecessary. The reaction time is usually from about 30 minutes to about 10 hours.

In the case of the continuous system, a moving bed and a fixed bed are usable, but the latter is particularly convenient. The feed rate of the raw materials is from 0.05 to 30 g of the total materials per gram of the catalyst per hour, preferably from 0.2 to 10 g of the total materials per gram of the catalyst per hour. In this case, the catalyst containing phosphoric acid or its condensate before reactivation is preferably supported on a carrier such as silica, alumina, silica-alumina, diatomaceous earth or clay. The more preferable carrier is silica. In case the reaction product of phosphoric acid and a titanium compound or a zirconium compound is used as the catalyst, it is preferred that the strength of the catalyst is increased by using the carrier.

The separation of the product from the reaction solution can be easily effected by, for example, distillation. In this case, separated ammonia, ethylenediamine and monoethanolamine can be returned to the reaction vessel and then reused therein.

The reactivation of the catalyst is accomplished by adding a phosphorus-containing material to the catalyst. For example, the reactivation process comprises the steps of dissolving or suspending the phosphorus-containing material in a solvent, immersing the catalyst in the resulting solution, draining, and then drying the catalyst. Examples of the solvent include water, methyl alcohol, ethyl alcohol, isopropyl alcohol and monoethanolamine.

No restriction is put on the drying temperature for the catalyst, and the temperature is usually from 10° to 700° C., preferably 50° to 200° C. After drying, the catalyst may be calcined, but this operation is not essential. When the drying is carried out at a temperature of 10° to 400° C., the drying is usually carried out in nitrogen, argon or the like and preferably in the absence of oxygen. When the drying is done at 400° C. or more, oxygen may be present in the atmosphere, because organic materials adhering to the catalyst can be burned out. No particular restriction is put on the drying time, but it is usually from about 1 to about 10 hours.

The reactivation of the catalyst can be achieved without removing it from the reaction vessel, in case the fixed bed system is employed.

When at least one of ammonia and ethylenediamine is reacted with monoethanolamine by the batch system, the catalyst as well as the phosphorus-containing material may be added to the reaction system in order to prepare the acyclic ethyleneamines simultaneously with reactivating the catalyst.

In the reactivation step of the catalyst, the amount of the phosphorus-containing material to be added depends upon the phosphorus/metal atomic ratio of the desired catalyst (when the pore volume, the phosphorus/metal ratio of the catalyst and the like are decided, the amount of the phosphorus-containing material to be added can be calculated).

Moreover, the catalyst can also be reactivated by first subjecting the catalyst to a heat treatment with a gas containing oxygen in order to burn out the organic materials adhering to the catalyst at a temperature of from 400° to 600° C., and then adding the phosphorus-containing material to the catalyst. However, this heat treatment is not always necessary.

Now, the present invention will be described in detail in reference to examples. However, the scope of the present invention should not be limited to these examples.

EXAMPLE 1

Catalyst 172.94 g of 85% phosphoric acid was added to 39.95 g of titanium dioxide, and the mixture was then kneaded. Next, 97.61 g of fine silica gel and 190 g of water were added thereto, followed by kneading and extruding (diameter = 3 mm). Afterward, the extruded materials were dried at 150° C. for 3 hours and then calcined at 500° C. for 5 hours. The thus-prepared catalyst was cut into a length of 3 mm.

A stainless steel reaction vessel having an inner diameter of 25.8 mm was packed with 54.84 g of the above-mentioned catalyst. Monoethanolamine and ammonia were then fed thereto at 13.5 g/hour and 56.5 g/hour, respectively, and reaction was carried out at a temperature of 280° C. under a pressure of 400 kg/cm² for 4,000 hours. Afterward, the reaction vessel was cooled so as to bring the reaction to an end, and the catalyst was withdrawn. It was confirmed that the performance of the catalyst deteriorated. The withdrawn catalyst (hereinafter referred to as "catalyst A") was used in the following test (P/Ti ratio before the reaction = 3.00, P/Ti ratio after the reaction = 1.55).

Reaction

A reaction pipe having an inner diameter of 10 mm and a length of 766 mm was packed with 10 g of the catalyst A the performance of which had deteriorated. Monoethanolamine (containing 500 ppm by weight of triethyl phosphate in terms of phosphorus) in which triethyl phosphate was dissolved and ammonia were added thereto at 2.46 g/hour and 10.30 g/hour, respectively, and reaction was then carried out at a temperature of 280° C. under a pressure of 400 kg/cm². The results are set forth in Table 1.

TABLE 1

| Passed Time (hr) | Conversion of Monoethanolamine (%) | Selectivity of Three Components* (%) |
|---|---|---|
| Shortly after starting | 22.0 | 52.6 |
| 78 | 34.0 | 67.8 |
| 164 | 42.5 | 73.6 |
| 360 | 51.7 | 86.1 |

*Note:
The three components were ethylenediamine, diethylenetriamine and triethylenetetramine.
Selectivity of Three Components = (mole of monoethanolamine converted into the three components)/(mole of monoethanolamine consumed in the reaction) × 100

EXAMPLE 2

Reaction

A reaction pipe having an inner diameter of 10 mm and a length of 766 mm was packed with 10 g of the catalyst A. Monoethanolamine in which triethyl phosphate was dissolved (so as to obtain a material containing 500 ppm by weight of triethyl phosphate in terms of phosphorus), ethylenediamine and ammonia were added thereto at 1.97 g/hour, 2.53 g/hour and 8.26 g/hour, respectively, and reaction was then carried out at a temperature of 280° C. under a pressure of 400 kg/cm². The results are set forth in Table 2.

TABLE 2

| Passed Time (hr) | Conversion of Monoethanolamine (%) | Selectivity of Three Components* (%) |
|---|---|---|
| Shortly after starting | 24.2 | 56.8 |
| 78 | 37.4 | 70.5 |
| 168 | 46.8 | 76.1 |
| 360 | 56.9 | 87.6 |

*Note:
The three components were ethylenediamine, diethylenetriamine and triethylenetetramine.
Selectivity of Three Components = (mole of monoethanolamine converted into the three components)/(mole of monoethanolamine consumed in the reaction) × 100

EXAMPLE 3

Reactivation of the Catalyst 10 g of the above-mentioned catalyst A (which had been dried in a nitrogen gas stream at 120° C. for 3 hours) whose performance had deteriorated was immersed for 3 hours in 20 cc of an aqueous phosphoric acid solution containing 11.0 g of phosphoric acid. The catalyst was then taken out from the solution, drained, and then dried at 120° C. for 3 hours in a nitrogen gas stream in order to reactivate the catalyst (P/Ti atomic ratio = 2.95).

Reaction

A reaction pipe having an inner diameter of 10 mm and a length of 766 mm was packed with 10 g of the reactivated catalyst. Monoethanolamine and ammonia were fed to the reaction pipe at 2.46 g/hour and 10.30 g/hour, respectively, and reaction was then carried out at a temperature of 280° C. under a pressure of 400 kg/cm². The results are set forth in Table 3.

COMPARATIVE EXAMPLE 1

Reaction was carried out under the same conditions as in Example 3 except that the unreactivated catalyst A having a deteriorated performance was used in an amount of 10 g. The results are set forth in Table 3.

REFERENCE EXAMPLE 1

Reaction was carried out under the same conditions as in Example 3 except that the new catalyst which had not been subjected to the reaction for 4,000 hours was used in an amount of 10 g. The results are set forth in Table 3.

TABLE 3

| | Conversion of MEA (%) | Selectivity (%) | | | |
|---|---|---|---|---|---|
| | | EDA | DETA | TETA | Three Components |
| Example 3 | 56.7 | 50.7 | 28.2 | 9.4 | 88.3 |
| Comp. Ex. 1 | 22.0 | 40.5 | 9.8 | 2.3 | 52.6 |
| Ref. Ex. 1 | 61.0 | 50.9 | 28.3 | 9.5 | 88.7 |

MEA ... monoethanolamine
EDA ... ethylenediamine
DETA ... diethylenetriamine
TETA ... triethylenetetramine
Three components ... EDA + DETA + TETA
Selectivity of Three Components = (mole of monoethanolamine converted into the three components)/(mole of monoethanolamine consumed in the reaction) × 100

EXAMPLE 4

Catalyst

A stainless steel reaction vessel having an inner diameter of 25.8 mm was packed with 54.84 g of a new catalyst which had been prepared in accordance with the same procedure as in Example 1 Monoethanolamine, ammonia and ethylenediamine were then fed thereto at 10.8 g/hour, 45.3 g/hour and 13.9 g/hour, respectively, and reaction was carried out at a temperature of 280° C. under a pressure of 400 kg/cm² for 4,000 hours. Afterward, the reaction vessel was cooled so as to bring the reaction to an end, and the catalyst was withdrawn.

The P/Ti atomic ratio of this withdrawn catalyst (hereinafter referred to as "catalyst B") was 1.80 (P/Ti atomic ratio before the reaction=3.00).

Reactivation of the Catalyst 10 g of the above-mentioned catalyst B (which had been dried in a nitrogen gas stream at 120° C. for 3 hours) having a deteriorated performance was immersed for 3 hours in 20 cc of an aqueous phosphoric acid solution containing 9.04 g of phosphoric acid. The catalyst was then taken out from the solution, drained, and then dried at 120° C. for 3 hours in a nitrogen gas stream in order to reactivate the catalyst (P/Ti atomic ratio=2.95).

Reaction

A reaction pipe having an inner diameter of 10 mm and a length of 766 mm was packed with 10 g of the reactivated catalyst. Monoethanolamine, ammonia and ethylenediamine were fed to the reaction pipe at 1.97 g/hour, 8.26 g/hour and 2.53 g/hour, respectively, and reaction was then carried out at a temperature of 280° C. under a pressure of 400 kg/cm². The results are set forth in Table 4.

COMPARATIVE EXAMPLE 2

Reaction was carried out under the same conditions as in Example 4 except that the unreactivated catalyst B having a deteriorated performance was used in an amount of g. The results are set forth in Table 4.

REFERENCE EXAMPLE 2

Reaction was carried out under the same conditions as in Example 4 except that the new catalyst before the reaction for 4,000 hours was used in an amount of 10 g. The results are set forth in Table 4.

TABLE 4

| | Conversion of MEA (%) | Selectivity (%) | | | |
| --- | --- | --- | --- | --- | --- |
| | | EDA | DETA | TETA | Three Components |
| Example 4 | 63.9 | 3.0 | 72.4 | 14.4 | 89.8 |
| Comp. Ex. 2 | 39.6 | 10.5 | 49.7 | 10.3 | 70.5 |
| Ref. Ex. 2 | 66.2 | 3.0 | 72.7 | 14.5 | 90.2 |

TABLE 4-continued

MEA ... monoethanolamine
EDA ... ethylenediamine
DETA ... diethylenetriamine
TETA ... triethylenetetramine
Three components ... EDA + DETA + TETA
Selectivity of Three Components = (mole of monoethanolamine converted into the three components)/(mole of monoethanolamine consumed in the reaction) = 100

As described in Tables 1 and 2, it is confirmed that the performance of the catalyst and the selectivity of the three components can be improved, when at least one of ammonia and ethylenediamine is reacted with monoethanolamine by the use of the catalyst having a deteriorated performance which has been utilized in the reaction between ammonia and monoethanolamine, while a phosphorus-containing material (triethyl phosphate) is fed to the catalyst bed. That is, in case at least one of ammonia and ethylenediamine is reacted with monoethanolamine, using an inactivated catalyst (after the reaction, phosphoric acid components are extracted into the solution, and the content of these components in the catalyst is lower than before the reaction) or a new catalyst in the fixed bed in order to prepare the acyclic ethyleneamines, a phosphorus-containing material is fed to the catalyst bed during the reaction, whereby the performance of the catalyst can be improved and the life of the catalyst can be prolonged.

Furthermore, as is apparent from the conversion of monoethanolamine and the selectivity of the three components described in Tables 3 and 4, when phosphoric acid is added to the catalyst having a deteriorated performance which has been used in the reaction of at least one of ammonia and ethylenediamine with monoethanolamine, the catalyst can be reactivated up to the same level as the new catalyst.

What is claimed is:

1. A process for the preparation of acyclic ethyleneamines which comprises reacting at least one of ammonia and ethylenediamine with monoethanolamine at 150°–400° C. at 1–1000 kg/cm² in the presence of a fixed bed catalyst containing at least one compound selected from the group consisting of phosphoric acid, pyrophosphoric acid, triphosphoric acid, polyphosphoric acid, ammonium phosphate, ammonium pyrophosphate and ammonium triphosphate, and metallic salts of phosphoric acid, pyrosphosphoric acid, triphosphoric acid and polyphosphoric acid, wherein 1–50 moles of ammonia and 0.1–10 moles of ethylenediamine are used per mole of monoethanolamine, while 1–1000 ppm (by weight) of a phosphorus-containing material in terms of phosphorus per monoethanolamine is supplied to said catalyst bed.

2. The process for the preparation of acyclic ethyleneamines according to claim 1 in which the phosphorus-containing material is supplied to said catalyst bed in an amount of 10–1000 ppm (by weight) in terms of phosphorus per monoethanolamine.

* * * * *